(12) United States Patent
Kühn et al.

(10) Patent No.: US 7,934,432 B2
(45) Date of Patent: May 3, 2011

(54) METHOD FOR MEASURING THE RUN TIME OF AN ULTRASONIC PULSE IN THE DETERMINATION OF THE FLOW VELOCITY OF A GAS IN A BREATHING GAS VOLUME FLOW SENSOR

(75) Inventors: Henning Kühn, Buchholz i. d. N (DE); Henning Gerder, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 766 days.

(21) Appl. No.: 11/968,958

(22) Filed: Jan. 3, 2008

(65) Prior Publication Data
US 2008/0208056 A1    Aug. 28, 2008

(51) Int. Cl.
*G01F 1/66* (2006.01)
(52) U.S. Cl. .................................. 73/861.28
(58) Field of Classification Search ... 73/861.26–861.28
See application file for complete search history.

(56) References Cited

U.S. PATENT DOCUMENTS

| 5,461,931 | A | 10/1995 | Gill | |
| 7,152,490 | B1 * | 12/2006 | Freund et al. | 73/861.27 |
| 7,673,527 | B2 * | 3/2010 | Ehring et al. | 73/861.28 |

FOREIGN PATENT DOCUMENTS
EP     0 347 096 A2    12/1989
* cited by examiner

*Primary Examiner* — Jewel Thompson
(74) *Attorney, Agent, or Firm* — McGlew and Tuttle, P.C.

(57) ABSTRACT

A method is provided for measuring the run time of an ultrasonic pulse in the determination of the flow velocity of a gas in a breathing gas volume flow sensor (1). The breathing gas volume flow sensor (1) has a flow duct (3) with a measuring section, wherein the measuring section is arranged in parallel to or at an angle ($\alpha$) smaller than 90° to the flow duct (3). The measuring section has an ultrasound transmitter (5) and an ultrasound receiver (7). The method determines the run time of the ultrasonic pulse from the receiving signal spectrum without the damping of the ultrasonic pulse having an effect on the run time measurement by an ultrasonic pulse being triggered by a transmitting pulse at the ultrasound transmitter (5). The ultrasound receiver (7) sends a receiving signal and the receiving signal is recorded as a first receiving signal data record as a function of time after the transmitting pulse. A correlation function of the first receiving signal data record is formed with the first sample data record. The run time of the ultrasonic pulse is determined from the point in time of the correlation maximum.

22 Claims, 3 Drawing Sheets

METHOD FOR MEASURING THE RUN TIME OF AN ULTRASONIC PULSE IN THE DETERMINATION OF THE FLOW VELOCITY OF A GAS IN A BREATHING GAS VOLUME FLOW SENSOR

CROSS REFERENCE TO RELATED APPLICATIONS

This application claims the benefit of priority under 35 U.S.C. §119 of German Patent Application 10 2007 009 432.0 filed Feb. 27, 2007, the entire contents of which are incorporated herein by reference.

FIELD OF THE INVENTION

The present invention pertains to a method for measuring the run time of an ultrasonic pulse in the determination of the flow velocity of a gas in a breathing gas volume flow sensor, wherein the breathing gas volume flow sensor has a flow duct with a measuring section, wherein the measuring section is arranged in parallel to or at an angle smaller than 90° to the flow duct, and wherein the measuring section has an ultrasound transmitter and an ultrasound receiver.

BACKGROUND OF THE INVENTION

The determination of the volume flow of breathing gases is of considerable relevance in the area of anesthesia devices and respirators, because, for example, the absolute quantity of an anesthetic supplied to a patient during anesthesia can be derived therefrom. The absolute quantity supplied of an anesthetic is, in turn, a critical parameter in anesthesia, which should be known as precisely as possible. Therefore, it is important, particularly in medical engineering, to determine this variable as exactly as possible.

To determine the breathing gas volume flow, hot wire anemometers are known from the state of the art, which operate in such a way that the resistance of a hot wire, which is arranged in the breathing gas flow, is determined. Here, the hot wire is made of a material that has a temperature-dependent resistance. The extent to which the hot wire is cooled by the gas flow depends on the volume flow and thus on the flow velocity, so that the resistance of the hot wire is an indication of the flow velocity. However, a drawback of this method is that the hot wire itself exhibits a flow resistance and that, furthermore, only the absolute value of the flow velocity can be determined from the resistance of the hot wire. Information about the direction of flow is not possible, however.

As an alternative to hot wire anemometry, it has become known, for example, from EP 0 347 096 A2 to use the run time of ultrasonic pulses that pass through a measuring section with an ultrasound transmitter and an ultrasound receiver, which measuring section runs in parallel to the flow duct, to measure the flow velocity of gases. Here, the run time of the ultrasonic pulse is measured both against the direction of flow and with the direction of flow, and the flow velocity and its direction are determined from the run time difference.

However, problems arise in the measurement of the run times. To determine the point in time, at which the ultrasonic pulse impacts the receiver, a level has to be set, which is used as the stop level, so that the time measurement is stopped when the level of the signal of the receiver exceeds this stop level. However, in contrast to liquids, the difficulty arises that the damping which the ultrasonic pulse experiences in the gas flow varies greatly. This in turn results in that inaccuracies occur in the determination of the point in time of the impact on the receiver, since the stop level is exceeded only relatively "late," for example, in case of a strong damping.

To this end, EP 0 347 096 A2 suggests adding a phase jump into the signal sent by the ultrasound transmitter, which can be used as a marker and whose impact can be detected by the receiver as a stop signal. However, the drawback of this type of method is that this can be carried out only at relatively long sound paths. Moreover, the problem arises in case of strong dampings that either the amplitude, with which the ultrasound transmitter transmits the signal, or the amplification of the signal of the receiver has to be increased or adapted.

Another fundamental problem in the measurement of the run time of the ultrasonic pulse is that the measured run time between the transmitting pulse at the ultrasound transmitter sent by the control electronics and the reception of the ultrasonic pulse at the receiver includes a delay in the transmission of the pulse, i.e., a delay time between the transmitting pulse at the ultrasound transmitter and the actual transmission of the signal by the ultrasound transmitter.

If it is intended to determine this delay, the exact length of the measuring section is needed in case of known sound velocity of the gas. Furthermore, the exact measuring section length is necessary for an accurate calibration. However, the further problem arises here that, on the one hand, there are tolerances in the manufacture of the flow ducts and the measuring section length is thus only known with a certain inaccuracy. On the other hand, a cleaning of the flow duct connected with the assembly and disassembly of the ultrasound transmitter and of the ultrasound receiver may lead to a change in the measuring section length. Therefore, it is desirable for an exact measurement of the flow velocity to provide a method that makes it possible to use the exact measuring section length during operation. It is thus advantageous to determine the exact measuring section length before or during the measuring operation in a routine (initialization).

Another difficulty in the determination of the flow velocity from the measured run times is that the flow velocity can be determined from the run times basically only with the knowledge of the sound velocity. However, if the composition of the breathing gas or its temperature changes, for example, in a respirator that is used for anesthesia, the sound velocity in the breathing gas also changes.

Thus, besides the run time measurement, another measurement of the current sound velocity would have to occur for the determination of the flow velocity. To this end, it has become known from U.S. Pat. No. 5,461,931 to measure the run time of an ultrasonic pulse and thus to determine the sound velocity in an area of the sensor, in which the flow rests. However, this is very expensive.

In the exceptional case in which measuring sections have exactly the same length, the determination of the flow velocity against and with the flow from the run times becomes independent from the sound velocity. This can be done only with great difficulty in a sensor that uses two measuring sections for the two directions, which results, on the one hand, from the manufacturing tolerances as well as the assembly quality and, on the other hand, from changes in the disassembly and assembly before and after the cleaning.

SUMMARY OF THE INVENTION

Therefore, it would be desirable to provide a method of analysis that is capable of determining the flow velocity from the measured run times of ultrasonic pulses that have been measured along two measuring sections with slightly deviating length, without the knowledge of the sound velocity being necessary for this purpose.

Therefore, starting from the state of the art, the object of the present invention is to provide a method to determine the run time of ultrasonic pulses from the receiving signal spectrum of the ultrasound receiver as a function of time after the transmitting pulse at the ultrasound transmitter, without the damping of the ultrasonic pulses having an effect on the run time measurement.

This object is accomplished by a method for measuring the run time of an ultrasonic pulse in the determination of the flow velocity of a gas in a breathing gas volume flow sensor, wherein the breathing gas volume flow sensor has a flow duct with a measuring section, wherein the measuring section is arranged in parallel to or at an angle smaller than 90° to the flow duct and wherein the measuring section has an ultrasound transmitter and an ultrasound receiver, wherein in the method:

- an ultrasonic pulse is triggered by a transmitting pulse at the ultrasound transmitter;
- the ultrasound receiver sends a receiving signal;
- the receiving signal is recorded as a first receiving signal data record as a function of time after the transmitting pulse;
- the correlation function of the first receiving signal data record is formed with a first sample data record; and
- the run time of the ultrasonic pulse is determined from the point in time of the correlation maximum.

In contrast to the state of the art, a stop level, which is used as a threshold that has to be exceeded by the amplitude of the signal sent by the receiver in order to set the stopping point in time of the measurement, is not used in the method according to the present invention. Rather, the run time is determined by a processing of the receiving signal by means of correlation.

To this end, after the triggering of an ultrasonic pulse, which runs from the ultrasound transmitter to the ultrasound receiver, the receiving signal of the ultrasound receiver is first recorded as a function of time as a first receiving signal data record. The correlation function is then formed between this first receiving signal data record and a sample data record.

In general, the values of the correlation function $A(\tau)$ between a first function $E(t)$ and a second function $F(t)$ result according to $$A(\tau) = \int E(t)F(t+\tau)dt,$$

in which $\tau$ is the shift between the functions. In the case of data records $s(t)$ and $g(t)$, which contain measured values, each of which was picked up after distinct time intervals, such as may be the case, for example, in the first receiving signal data record, the values of the correlation function $p^E_{sg}$ may be determined as follows $$p^E_{sg}(m) = \frac{\sum_{n=-\infty}^{\infty} s(nT) \cdot g(nT+m)}{\sqrt{E_s \cdot E_g}}$$

in which E is the respective signal energy and is generally calculated for a data record a according to $$E_a = \sum_{n=-\infty}^{\infty} a(nT)$$

m is again the shift in this case.

However, the correlation function may also be formed in such a way that the Fourier transform of the data records are at first determined, these are multiplied with one another and subsequently the result is transformed back. Thus, the present invention is not limited to calculating the correlation function exclusively in the time domain.

In the method according to the present invention, the correlation function is formed between the first receiving signal data record and a sample data record, wherein the sample data record has the pattern of the signal of the ultrasound receiver, which is produced in the impact of the ultrasonic pulse on the receiver. In the sample data record, the point in time that corresponds to the impact of the ultrasonic pulse on the receiver coincides either with the point in time of the triggering pulse or has a defined time interval thereto.

If the correlation function is formed between this sample data record and the first receiving signal data record, a maximum of the correlation function arises in the time shift or the point in time, at which the part of the sample data record that corresponds to the impact of the ultrasonic pulse on the receiver coincides with the corresponding section in the receiving signal data record. Therefore, this time shift or this point in time represents an indicator of the run time of the ultrasonic pulse.

Thus, when, conversely, the position of the maximum of the correlation function is determined, the run time can be determined therefrom without it being necessary to set a stop level. In particular, the determined run time is thus independent of the damping of the signal along the measuring section, and the run time is determined directly from the receiving signal data record.

The method according to the present invention for measuring the run time of an ultrasonic pulse can be used, on the one hand, in breathing gas volume flow sensors, which have only one measuring section, wherein a first run time for an ultrasonic pulse in parallel to the direction of flow and a second run time for an ultrasonic pulse against the direction of flow are determined one after the other. On the other hand, the method can be used in sensors, which have two measuring sections, in which the two run times can be determined at the same time.

In a preferred embodiment of the method, the sample data record is taken from the first receiving signal data record, wherein this may, furthermore, preferably take place by the maximum of the first receiving signal data record being determined and by the sample data record containing a section about the maximum.

In order to reduce the memory needed for the first receiving signal data record and in particular in order to reduce the calculation effort in the calculation of the values of the correlation function, it is preferred if the first receiving signal data record is recorded from a point in time that is arranged at a spaced location from the point in time of the transmitting pulse by a triggering delay. Here, the triggering delay is selected such that it is somewhat shorter than the time that an ultrasonic pulse needs under optimal conditions, i.e., at maximum conceivable sound velocity, to reach from the sender to the receiver.

According to another preferred embodiment of the method:

- a second ultrasonic pulse is triggered by a transmitting pulse at the ultrasound transmitter;
- the ultrasound receiver sends a receiving signal;
- the receiving signal is recorded as a second receiving signal data record as a function of time after the transmitting pulse;
- the correlation function of the second receiving signal data record is formed with the first sample data record; and
- the first sample data record is scaled.

In this case, the sample data record used, which may be taken, for example, from the first receiving signal data record, is resealed at the signal height so as to take into consideration, for example, a changed damping of the ultrasonic pulse along the path section. Thus, the first sample data record may be scaled in proportion to the ratio of the signal energies of the first and the second receiving signal data records.

According to another preferred embodiment of the method;

a second ultrasonic pulse is triggered by a transmitting pulse at the ultrasound transmitter;

the ultrasound receiver sends a receiving signal;

the receiving signal is recorded as a second receiving signal data record as a function of time after the transmitting pulse;

the correlation function of the second receiving signal data record is formed with a second sample data record;

wherein a section of the first receiving signal data record, which is arranged at a spaced location from the point in time of the transmission of the ultrasonic pulse by the run time determined from the first receiving signal data record, is used as the second sample data record; and the run time of the second ultrasonic pulse is determined from the point in time of the correlation maximum.

In this exemplary embodiment of the method according to the present invention, the sample data record that is correlated with the second receiving signal data record is taken from the first receiving signal data record in the area that coincides with the point in time of the impact of the ultrasonic pulse on the ultrasound receiver.

So that the sample data record constantly decreases to zero at the edges and so that no artifacts are produced in the formation of the correlation function, the sample data record may be folded with a window function (Hamming window, Blackman-Harris window).

Thus, a section, of which it is expected that it is very similar to the section of the second receiving signal spectrum, which corresponds to the impact of the ultrasonic pulse on the receiver, is used as the sample data record. This in turns results in that the maximum of the correlation function, which is formed for the second modified receiving signal spectrum, is more clearly defined.

Moreover, an adaptive method, in which the similarity of the sample data record is further improved in relation to the desired section, is provided with this preferred embodiment. Furthermore, this method makes it possible for the sample data record to be adapted correspondingly to the signal of the impacted ultrasonic pulse, so that changes in the pattern of the signal or in the amplitude, which come from a change in the gas composition or in the gas temperature, are automatically taken into consideration.

While the sample may be adapted by automatically taking from a data record that is earlier in time, it is, however, also conceivable to take into consideration the value of the standardized correlation coefficients or the change in the signal energy as well as the change in the sound velocity as an indicator of a damping of the signal (gas type effect). Because of this indicator, an adaptation of the sample data record can then take place in a case-specific manner, for example, by means of an overwriting by a chronologically newer sample data record from a signal data record or even by a scaling of the signal amplitude.

More preferably, the second receiving signal data record may also be recorded from a point in time that is arranged at a spaced location from the point in time of the transmitting pulse by a triggering delay, so that the calculating effort for the calculation of the correlation function is in turn reduced, since this can take place in a smaller time window.

Another preferred exemplary embodiment of the method according to the present invention provides that:

an ultrasonic pulse is triggered by a transmitting pulse at the ultrasound transmitter, the ultrasound receiver sends a receiving signal;

the receiving signal is recorded as a delay-time receiving signal data record as a function of time after the transmitting pulse;

the correlation function of the delay-time receiving signal data record is formed with a delay-time sample data record;

the time difference between the transmitting pulse and the first reception of the ultrasonic pulse is determined from the point in time of the correlation maximum;

the delay time between the transmitting pulse and the transmission of the ultrasonic pulse is determined by subtracting the signal run time for the ultrasonic pulse along the length of the measuring section; and the signal run time is calculated from the measuring section length.

In particular, the delay-time sample data record can be taken here from the delay-time receiving signal data record, wherein the maximum of the delay-time receiving signal data record is determined and the delay-time sample data record includes a section around the maximum.

In this exemplary embodiment of the method according to the present invention, the correlation is used for determining the delay time that lies between the transmitting pulse and thus the zero point in time of the data record and the actual transmission of the ultrasonic pulse by the transmitter, in resting gas with known sound velocity in the sensor from the delay-time receiving signal spectrum. With knowledge of the delay time, it is possible to determine the "pure" signal run times, which in turn makes it possible to determine the flow velocity even in the case that a breathing gas volume flow sensor has two measuring sections, whose lengths differ from one another, without the knowledge of the value of the sound velocity being necessary. However, this will be dealt with in more precise terms below.

More preferably, the length of the measuring section is determined in the method according to the present invention in such a way that:

an ultrasonic pulse is triggered by a transmitting pulse at the ultrasound transmitter, the ultrasound receiver sends a receiving signal;

the receiving signal is recorded as a measuring-section receiving signal data record as a function of time after the transmitting pulse;

the autocorrelation of the measuring-section receiving signal data record is formed;

the time interval between the first reception of the ultrasonic pulse at the ultrasound receiver and the reception of the first echo of the ultrasonic pulse is determined from the autocorrelation of the measuring-section receiving signal data record; and the measuring section length is calculated from the time interval and the sound velocity.

In this preferred embodiment of the method, the length of the measuring section is determined by means of autocorrelation, wherein, in case of gas resting in the breathing gas volume flow sensor with known sound velocity, a measuring-section receiving signal data record is picked up over a time span that is sufficient for not only the first impact of the ultrasonic pulse on the receiver to be determined, but also for the impact of the first echo, which is formed by the ultrasonic pulse being reflected to the transmitter in the first impact, to be reflected from this ultrasonic pulse and to be impacted again on the receiver.

In the formation of the autocorrelation, the functions $s(t)$ and $g(t)$ contained in the formula indicated above are identical, so that, when the autocorrelation of this measuring-section receiving signal data record is determined, besides the maximum at a shift t=0, two other maxima arise at $\tau=\pm\Delta T_{MS}$. In this case, $\Delta T_{MS}$ is the time that the ultrasonic pulse needs, after the first impact on the receiver, to run from this receiver again to the transmitter and back to the receiver.

By using autocorrelation in combination with the first echo, the run time for passing through the two measuring sections can be determined without a delay time or the like entering into the result.

Thus, this preferred embodiment of the method makes it possible to exactly determine the length of the respective measuring section, in each case before the beginning of the actual volume flow measurement in resting gas in the sensor, which forms the basis for the further determinations of delay times and volume flows.

Since the sound velocity, which is needed in the determination of the measuring section length, depends on the temperature of the gas, the temperature of the gas in the breathing gas volume flow sensor is determined in a preferred embodiment of the method according to the present invention.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiment of the invention is illustrated.

DESCRIPTION OF THE PREFERRED EMBODIMENT

Referring to the drawings in particular at first, the design of a breathing gas volume flow sensor 1 with a flow duct 3 is described with reference to FIGS. 1 and 2. The breathing gas volume flow sensor 1 in this preferred exemplary embodiment has two measuring sections, which run at an angle to the flow duct 3.

The first measuring section has a first ultrasound transmitter 5 and a first ultrasound receiver 7, while the second measuring section has a second ultrasound transmitter 9 and a second ultrasound receiver 11. In this case, each of the measuring sections runs at an angle to the flow duct 3, which is smaller than 90°, wherein the first measuring section has a length $L_1$ and the second measuring section has a length of $L_1+dL$.

When an ultrasonic pulse passes through the first measuring section, having flowed through the flow duct 3 from the first ultrasound transmitter 5 to the first ultrasound receiver 7, its velocity is increased because of the flow 13, while the velocity is reduced for an ultrasonic pulse that passes through the second measuring section between the second ultrasound transmitter 9 and the second ultrasound receiver 11. The flow velocity can be calculated from the run time difference resulting therefrom, as will still be explained below.

The arrangement with two measuring sections offers the advantage that the two run times can be determined at the same time. However, the present invention is not limited to such an arrangement with two measuring sections, but may also be used in a breathing gas volume flow sensor, which is not shown here, that has only one measuring section, at the ends of which is arranged a transducer each, so that run times for ultrasonic pulses can be measured in both directions along the measuring section. The transducers may operate here as transmitters and receivers at the same time, or they can be switched between transmitting and receiving mode.

The ultrasound transmitters 5, 9 are connected to a function generator 15, which is able to transmit a transmitting pulse at the ultrasound transmitters 5, 9, so that an ultrasonic pulse is triggered at each of the latter. Here, a delay time occurs between the transmitting pulse and the actual transmission of the ultrasonic pulse, the knowledge of which is relevant for the determination of the run times.

Finally, the breathing gas volume flow sensor 1 also comprises another signal processing unit 17 that records receiving signal data records from the signals of the ultrasound receivers 7, 11, i.e., records the amplitude of the starting signal of the ultrasound receivers 7, 11 as a function of time.

A preferred exemplary embodiment of the method according to the present invention runs as follows.

In a first step, the lengths of the first measuring section $L_1$ and the second measuring section $L_1+dL$ are determined. To this end, one proceeds in such a way that an ultrasonic pulse, which runs along the first measuring section to the first ultrasound receiver 7, is triggered by means of a transmitting pulse of the function generator 15 at the first ultrasound transmitter 5 in resting gas with known sound velocity C in the flow duct 3 of the breathing gas volume flow sensor 1. The first ultrasound receiver 7 sends a receiving signal, which is recorded as a measuring-section receiving signal data record 19 by the signal processing unit 17 as a function of time after the transmitting pulse.

Figure 3:
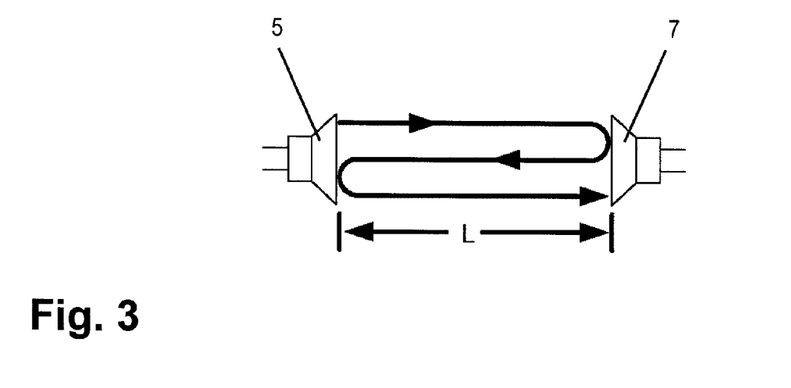
FIG. 3 is a schematic view of the run path of an ultrasonic pulse in the determination of the length of a measuring section.

In this case, the plotting takes place over a period of time that is sufficient for the ultrasonic pulse, as shown in FIG. 3, to run from the first ultrasound transmitter 5 to the first ultrasound receiver 7, to be reflected there, to run back to the first ultrasound transmitter 5 and to be reflected again to the first ultrasound receiver 7. Thus, both the first impact of the ultrasonic pulse at the first ultrasound receiver 7 and the impact of the first echo are determined in the measuring-section receiving signal data record 19 (see FIG. 4).

Such a measuring-section receiving signal data record 19 is schematically shown in FIG. 4a. The data record arises as follows. At the point in time 1 (zero point) the transmitting pulse is transmitted by the function generator 15. However, the delay time, whose determination will still be explained below, lies between the transmission of the transmitting pulse at the point in time 1 and the actual transmission of the ultrasonic pulse at the point in time 2. At the point in time 3 the ultrasonic pulse impacts on the first ultrasound receiver 7 for the first time. After the ultrasonic pulse has again run back to the first ultrasound transmitter 5, the first echo again impacts on the first ultrasound receiver 7 at the point in time 4.

In the analysis, the autocorrelation is formed at this measuring-section receiving signal data record 19. In this case, the measuring-section receiving signal data record $E_{MS}(t)$ 19 is correlated with itself, i.e., $E_{MS}(t)$ with $E_{MS}(t+m)$. To this end, the autocorrelation function $A_{MS}(m)$ is calculated at different time shifts m according to $$A_{MS}(m) = \frac{\sum_{n=0}^{k} E_{MS}(nT) \cdot E_{MS}(nT+m)}{E_{MS}}$$

wherein $$E_{MS} = \sum_{n=0}^{k} E_{MS}(nT)$$

applies, k is the number of scanned values in the measuring-section receiving signal data record 19 and T is the reciprocal value of the scanning rate.

It is immediately clear that the autocorrelation function $A_{MS}(m)$ has a maximum at m=0. Moreover, the autocorrelation function has other maxima at $m=\pm DT_{MS}$, since here the signal section, which corresponds to the first impact of the ultrasound pulse (point in time 3), overlaps with the signal section, which corresponds to the impact of the first echo (point in time 4).

The time interval $\Delta T_{MS}$ between the first impact of the ultrasonic pulse at the ultrasound receiver 7 and the impact of the first echo of the ultrasonic pulse is determined from the autocorrelation $A_{MS}(m)$ of the measuring-section receiving signal data record $E_{MS}(t)$ 19, wherein this is the interval of the maximum at m=0 and the secondary maxima, respectively.

The measuring section length $L_1$ is determined from this time interval $\Delta T_{MS}$ with the sound velocity C of the gas located in the flow duct 13. Since $\Delta T_{MS}$ corresponds to the run time for the twofold measuring section, the measuring section length results from $L_1 = \frac{1}{2} \cdot C \cdot \Delta T_{MS}$.

Since the temperature of the gas in the breathing gas volume flow sensor is determined by means of a temperature-measuring element (not shown) in the exemplary embodiment of the method according to the present invention, the temperature dependence of the sound velocity C may, moreover, be taken into consideration.

The run time for the passing through of the twofold measuring section can be determined by using autocorrelation in combination with the first echo, without a delay time or the like entering into the result. Thus, the length of the respective measuring section can be exactly determined in each case before the beginning of the actual volume flow measurement, so that small changes, which occur after a cleaning of the sensor with a disassembly connected therewith, do not have an effect on the measurement.

In the same manner as for the first measuring section, the length of the second measuring section $L_1+dL$ is also determined, so that subsequently both measuring section lengths for the actual volume flow measurement are known.

Figure 5:
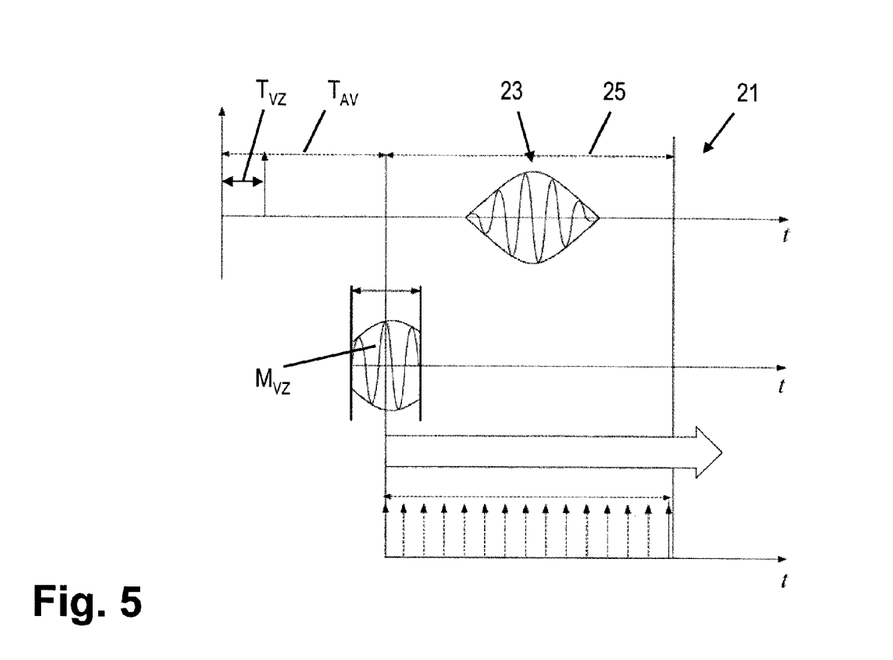
FIG. 5 is a schematic view of the resulting delay-time receiving signal data record for determining the delay time as well as its analysis.

In the next step of this preferred embodiment of the method according to the present invention, the respective delay times between the transmitting pulse of the function generator 15 and transmission of the ultrasonic pulses by the first and second ultrasound transmitters 5, 9 are likewise determined in resting gas with known sound velocity in the flow duct 3 with the now known measuring section lengths $L_1$ and $L_1+dL$, respectively. For, as shown in FIG. 5, there is a delay time $T_{VZ}$ between the transmitting pulse and the transmission of the ultrasonic pulse, wherein the receiving signal data record is, however, always recorded in relation to the transmitting pulse. If it is intended to obtain the pure signal run times for further processing of the data, these delay times have to be determined first.

In a first alternative for the determination of the delay time, at first an ultrasonic pulse is triggered by a transmitting pulse of the function generator 15 at the first ultrasound transmitter 5 in the first measuring section while the gas rests in the breathing gas volume flow sensor 1, wherein the ultrasonic pulse runs to the first ultrasound receiver 7. The first ultrasound receiver 7 then sends a receiving signal, which is recorded as a delay-time receiving signal data record 21 by means of the signal processing unit 17 as a function of time after the transmitting pulse (see FIG. 5).

The maximum is then set in the delay-time receiving signal spectrum 21, wherein the maximum 23 of the amplitude of the delay-time receiving signal spectrum 21 is used to this end. An area around the maximum 23 is subsequently taken from the delay-time receiving signal data record 21 as a delay-time sample data record $M_{VZ}$.

The correlation function $A_{VZ}$ of the delay-time receiving signal data record $(E_{VZ})$ (21) is then formed with the delay-time sample data record $M_{VZ}$, wherein this preferably takes place according to the equation $$A_{VZ}(m) = \frac{\sum_{n=0}^{k} E_{VZ}(nT) \cdot M_{VZ}(nT+m)}{\sqrt{M_{VZ} \cdot E_{VZ}}}.$$

As shown in the lower part of FIG. 5, the sample data record $M_{VZ}$ lies at a shift m=0 in a defined time interval to the transmitting pulse and is shifted with increasing shift m along the receiving signal data record 21 and the correlation is determined in each case.

The time difference $\Delta T_{VZ}$ between the transmitting pulse and the first reception of the ultrasonic pulse can then be determined from the point in time of the correlation maximum, i.e., the shift $m_{max}$, at which the maximum of the correlation function arises.

As shown in FIG. 5, the delay-time receiving signal data record 21 cannot be recorded from the transmitting pulse, but only within a scanning window 25, which begins from a point in time that is arranged at a spaced location from the point in time of the transmitting pulse by a triggering delay $T_{AV}$ in order to reduce the amount of data for the calculation of the correlation function.

In this case, the triggering delay $T_{AV}$ still has to be added to the shift $m_{max}$, in which the correlation maximum occurs, in order to determine the actual time difference $\Delta T_{VZ}$ between the transmitting pulse and the first reception of the ultrasonic pulse ($\Delta T_{VZ} = m_{max} + T_{AV}$).

Since the measuring section length $L_1$ was already determined beforehand and the sound velocity C of the gas located in the sensor is known, the delay time $T_{VZ}$ can be calculated from the time difference $\Delta T_{VZ}$ according to $$T_{VZ} = \Delta T_{VZ} - \frac{L_1}{C}.$$

The delay time for the second ultrasound transmitter and receiver 9, 11 is determined in the same manner, so that the delay times $T_{VZ}$ are now also determined. By knowing the delay time $T_{VZ}$, it is possible to determine the "pure" signal run times.

In a second alternative for determining the delay time, the measuring-section receiving signal data record 19 is used instead of a delay-time receiving signal data record. In this case, at first advantage is taken of the fact that the time interval between the main maximum and the second secondary maximum in the correlation function, i.e., the interval between $n_x$ and $n_z$ in FIG. 4, corresponds to the run time for the twofold measuring section length. Accordingly, half of this interval, i.e., the interval between $n_x$ and $n_y$ corresponds to the measuring section length itself.

Figure 4:
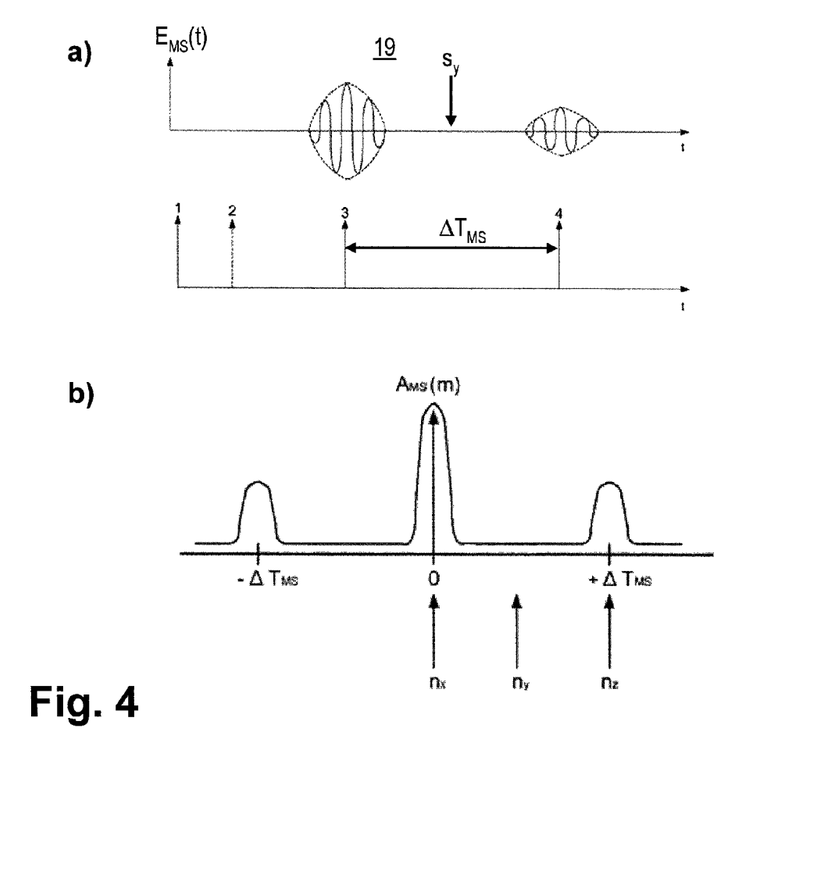
FIG. 4A is a schematic view of the resulting measuring-section receiving signal data record for determining the measuring section length
FIG. 4B is a view of the course of the corresponding autocorrelation function.

A point $s_y$ in the measuring-section signal data record 19 corresponds to the point $n_y$, wherein this point $s_y$ is arranged at a spaced location from the first maximum at the point in time 3 in FIG. 4 by the time span that the ultrasonic pulse needs from the ultrasound transmitter 5 to the ultrasound receiver 9.

When the part of the measuring-section receiving signal data record 19 that lies to the left of the point $s_y$ is then used as a sample data record, with which the correlation function is formed between this sample data record and the measuring-section receiving signal data record 19, the resulting correlation function has a maximum at a shift that is greater than $\Delta T_{MS}$, i.e., greater than twice the run time. For, the sample data record is not set at the point in time 2 in the measuring-section receiving signal data record 19, but rather the sample data record also has to be shifted via the delay time $T_{VZ}$, represented by the section between the point in time 1 and the point in time 2. Thus, the difference between $\Delta T_{MS}$ and the shift, at which a maximum occurs in the redetermined correlation function, is equal to the delay time $T_{VZ}$. Optionally, the triggering delay $T_{AV}$ still has to be added to the shift, at which the maximum occurs.

In the determination of the correlation function between the measuring-section receiving signal data record 19 and the sample data record generated therefrom, one proceeds in the same manner, as this was described in connection with the formation of the correlation function between the delay-time receiving signal data record 21 and the delay-time sample data record $M_{VZ}$. Therefore, the delay time can be determined in the method according to this second alternative, without an additional measurement having to be performed.

In order to set the point $s_y$ in the measuring-section receiving signal data record 19 in this second alternative, the area, viewed from the right in FIG. 4A, which leads to the secondary maxima at $\pm\Delta T_{MS}$ in the autocorrelation function $A_{MS}(m)$ shown in FIG. 4B, is at first faded out, so that the part of the measuring-section receiving signal data record 19 remains, which contains the signal, which arises due to the first impact of the ultrasonic pulse on the receiver 7 (area around the point in time 3). Subsequently, a point is passed in the measuring-section receiving signal data record 19, which is shifted by one-fourth of the width of the main maximum in the autocorrelation function at $n_x$ to the left of the point, at which the area ends, which leads to the secondary maxima at $\pm\Delta T_{MS}$. This point should then coincide with the middle of the signal, which occurs due to the first impact of the ultrasonic pulse (point in time 3). This should therefore be the case, because the width of the first main maximum in the autocorrelation function is twice as large as the width of the first maximum in the measuring-section receiving signal data record 19. Subsequently, a time span is again passed to the right, which corresponds to $\Delta T_{MS}/2$, i.e., the interval between $n_x$ and $n_z$. This is then the sought point $s_y$. The area to the left of $s_y$ in FIG. 4a is then used as a sample data record for the previously described determination of the autocorrelation function.

In order to determine the signal width of the main maximum at $n_x$ in the autocorrelation function $A_{MS}(m)$, one may proceed in a preferred embodiment such that the width of the area around the main maximum is determined, in which the autocorrelation function assumes a value that is greater than 10% of the value of the maximum. However, other methods may be used, in which, for example, the energy density is used.

After determining the measuring section lengths and the delay times, the actual measurement of the run times of the ultrasonic pulses along the first and second measuring sections may be carried out. The determination of the run time only for the first measuring section is explained below. The measurement for the second measuring section is carried out in an analogous manner, however.

To this end, an ultrasonic pulse is again triggered by a transmitting pulse of the function generator 15 at the first ultrasound transmitter 5, which runs to the first ultrasound receiver 7. The first ultrasound receiver 7 sends a receiving signal, which is recorded as a first receiving signal data record as a function of time after the transmitting pulse. As already in the determination of the delay time, the first receiving signal data record is not recorded already from the transmitting pulse, but only in a scanning window, which is arranged at a spaced location from the transmitting pulse by a triggering delay $T_{AV}$ in order to reduce the calculation effort.

The correlation function of the first receiving signal data record is then formed with a first sample data record. The sample data record may be the same sample data record $M_{VZ}$ that was already used within the framework of the determination of the delay time, i.e., the area about the maximum of the delay-time receiving signal data record 21. Analogously, the area around the maximum of the first receiving signal data record may also be used, however.

The correlation function is determined in the same manner, as this has already been explained in connection with the determination of the delay time $T_{VZ}$. The run time of the ultrasonic pulse can then be determined from the point in time or shift of the correlation maximum. The signal run time $T_{L1}$ for the first measuring section results from the shift $\Delta T_{L1}$ at which the correlation maximum occurs, by the equation $$T_{L1}=\Delta T_{L1}+T_{AV}-T_{VZ},$$

wherein the triggering delay $T_{AV}$ and the delay time $T_{VZ}$ are taken into consideration here.

Thus, the "pure" signal run time $T_{L1}$ of the ultrasonic pulse can be determined, knowing the delay time $T_{VZ}$, without it being necessary to set a stop level or the like in the signal processing unit 17.

The run time for the second measuring section $T_{L2}$ is determined in an analogous manner, so that the flow velocity can then be calculated.

While in the previously described determination of the run time of the ultrasonic pulse, the sample data record already used in the determination of the delay time $T_{VZ}$ was used as the sample data record, a section from the first receiving signal data record is used as the sample data record in the preferred embodiment of the method described here, in the second run time measurement following the first run time measurement.

To this end, one proceeds as follows. After the transmitting pulse has been sent by means of the function generator 15 at the first ultrasound transmitter 5, the receiving signal is again recorded as a second receiving signal data record as a function of time.

The correlation function of the second receiving signal data record is then formed with a second sample data record, wherein one proceeds likewise in the manner as was described in connection with the determination of the delay time.

However, in this preferred exemplary embodiment, a section of the receiving signal data record is used as a second sample data record, which is arranged at a spaced location from the point in time of transmitting the ultrasonic pulse by the run time determined from the first receiving signal data record. The run time of the second ultrasonic pulse is then determined from the point in time of the correlation maximum or from the corresponding shift.

Analogously, a section from the receiving signal data record determined directly beforehand or one lying chronologically before it can be used as a sample data record in any further measurement of the run time. Thus, the sample data record is adapted in this adaptive method, when the pattern of the signal, which is sent upon impact of the ultrasonic pulse, changes because of a change in the temperature or in the composition of the gas.

While the sample adaptation may take place, on the one hand, by taking from a chronologically earlier data record, it is also possible, as an alternative, to take into consideration, for example, the change in the signal energy as an indicator of a damping of the signal (gas type effect). Because of this indication, the sample data record can then be adapted in a case-specific manner, for example, by overwriting with a chronologically newer sample data record from a receiving signal data record.

Instead of using a new sample data record in the formation of the correlation function with the second, chronologically later receiving signal, the first sample data record may also be used, and this is scaled in the signal height in order to thus take into consideration, for example, a changed damping of the ultrasonic pulse along the path length. In this case, the first sample data record can be scaled in proportion to the ratio of the signal energies of the first and second receiving signal data records.

Within the framework of the exemplary embodiment described, the correlation functions are determined exclusively in the time domain. However, the correlation functions may also be formed in such a way that at first the Fourier transforms of the data records are determined, these are then multiplied with one another, and the result is then transformed back. The present invention is thus not limited to calculating the correlation function exclusively in the time domain.

The flow velocity in the breathing gas volume flow sensor 1 can be determined in a manner that is known per se from the run times along the first and second measuring sections. However, a special method is explained in detail below, in which knowledge of the sound velocity is not necessary.

This independent inventive method is not limited to an application within the framework of the previously described method in conjunction with the use of correlation, but rather can always be used if signal run times along measuring sections are related to one another, whose lengths may deviate from one another, for the determination of the flow velocity in the breathing gas volume flow sensor 1.

Figure 6:
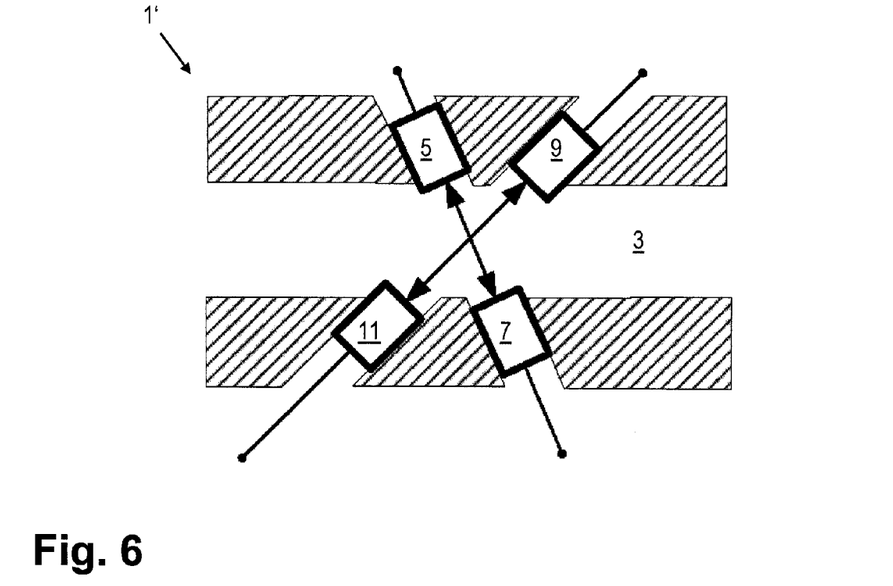
FIG. 6 is a schematic view of an alternative breathing gas volume flow sensor.

These length deviations may be, on the one hand, related to production, or arise from the geometry of the breathing gas volume flow. Such a geometry with different measuring sections may be necessary, if the sensor shall be arranged as close as possible to the patient and shall have a low dead volume that is not flushed through. FIG. 6 schematically shows a breathing gas volume flow sensor 1', in which the lengths of the measuring sections deviate from one another in a manner related to construction.

Figure 1:
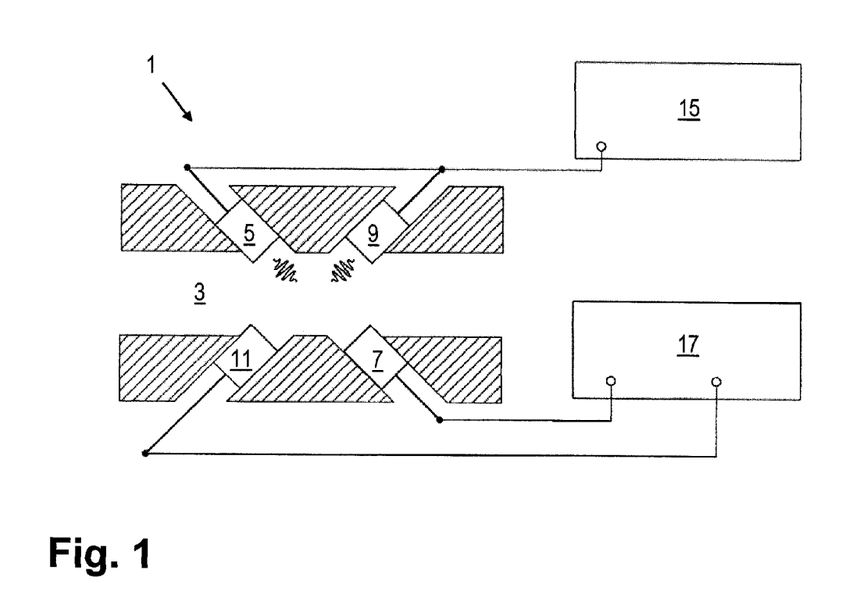
FIG. 1 is a schematic view of the design of a breathing gas volume flow sensor according to the invention.
Figure 2:
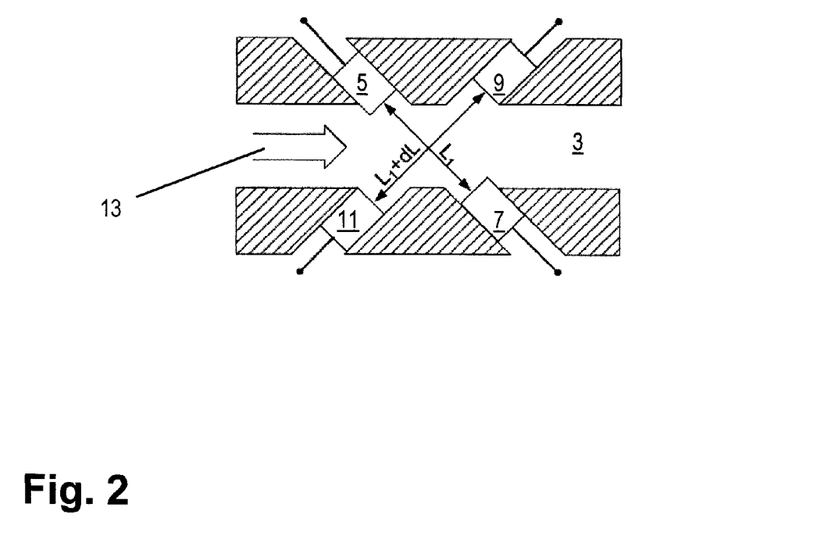
FIG. 2 is a view showing the length ratios of the measuring sections in a breathing gas volume flow sensor.

In a breathing gas volume flow sensor 1, 1', as it is shown in FIGS. 1, 2 and 6, the following equations arise for the run times of an ultrasonic pulse along the first and second measuring sections:

$$T_{L1} = \frac{L_1}{(C + v \cdot \cos(\alpha))} \quad (1)$$

$$T_{L2} = \frac{L_1 + dL}{C - v \cdot \cos(\alpha))1} \quad (2)$$

in which C is the sound velocity of the gas, a is the angle of the measuring sections in relation to the flow duct 3 and dL is the deviation of the measuring section lengths from one another. Finally, v is the sought flow velocity of the gas. The following equation arises for the flow velocity from these equations $$v = \frac{(T_{L2} - T_{L1})(L_1^2 + L_1 \cdot dL)}{(T_{L2} \cdot T_{L1}) \cdot (2 \cdot L_1 \cdot \cos(\alpha) + dL \cdot \cos(\alpha))} - \frac{dL \cdot C}{2 \cdot L_1 \cdot \cos(\alpha) + dL \cdot \cos(\alpha)}. \quad (3)$$

As this equation shows, it is necessary for the determination of the flow velocity v to know the sound velocity C of the gas, provided that the measuring section lengths deviate from one another, i.e., dL≠0. However, in a breathing gas, the composition, on the one hand, and the temperature, on the other hand, change, so that the sound velocity C likewise changes. Thus, it would be necessary to additionally measure this during the measurement, as this is described, for example, in U.S. Pat. No. 5,461,931 (which is hereby incorporated by reference).

In order to avoid this, the following approximation is made according to the present invention. If the so-called run time sum, i.e., $T_{L1}+T_{L2}$, is formed from equations (1) and (2), then the following approximation can be made for this with C>>v:

$$T_{L1} + T_{L2} = \frac{2 \cdot L_1 + dL}{C}. \quad (4)$$

If this is in turn inserted into equation (3) after C has been solved, the final formula results for the determination of the flow velocity $$v = \frac{(T_{L2} - T_{L1})(L_1^2 + L_1 \cdot dL)}{(T_{L2} \cdot T_{L1}) \cdot (2 \cdot L_1 \cdot \cos(\alpha) + dL \cdot \cos(\alpha))} - \frac{dL}{(T_{L1} + T_{L2}) \cdot \cos(\alpha)}. \quad (5)$$

This equation is also independent of the sound velocity in case of a difference between the measuring section lengths. However, it is necessary for using this equation that the "pure" signal run times be used in the measurement and not those that additionally still contain delay times. For, in such a case, errors would occur in the determination of the sound velocity with equation (5), and in particular caused by the distorted run time sum in the second term.

Thus, this determination method according to equation (5) can take advantage of the fact that both the "pure" run times and the exact measuring section lengths are measured according to the present invention, and equation (5) contains only known variables.

All in all, the present invention thus has the following advantages.

First, the determination of the measuring section length makes possible a recalibration before each beginning of a volume flow measurement as well as the exact determination of the delay time. This knowledge of the delay time in turn makes it possible to determine pure run times.

Moreover, it is made possible by the adaptive adaptation of the sample that the measurement method is adapted to different conditions, such as changing gas compositions or temperatures, which leads to a changed damping of the ultrasonic pulse along the measuring sections.

Finally, a method for determining the flow velocity by means of measuring the pure run times can be selected, which is independent of the sound velocity even at different measuring section lengths.

While specific embodiments of the invention have been shown and described in detail to illustrate the application of the principles of the invention, it will be understood that the invention may be embodied otherwise without departing from such principles.

What is claimed is:

1. A method for measuring the run time of an ultrasonic pulse in the determination of the flow velocity of a gas, the method comprising the steps of:
   providing a breathing gas volume flow sensor with a flow duct having a measuring section;
   arranging the measuring section in parallel to or at an angle smaller than 90° to the flow duct;
   providing the measuring section with an ultrasound transmitter and an ultrasound receiver;
   triggering an ultrasonic pulse at the ultrasound transmitter by a transmitting pulse such that the ultrasound receiver sends a receiving signal and the receiving signal is recorded as a first receiving signal data record as a function of time after the transmitting pulse;
   forming a correlation function of the first receiving signal data record with a first sample data record; and
   determining a run time of the ultrasonic pulse from the point in time of a correlation maximum.

2. A method in accordance with claim 1, wherein the sample data record is taken from the first receiving signal data record.

3. A method in accordance with claim 2, wherein the maximum of the first receiving signal data record is determined and the sample data record includes a section around the maximum.

4. A method in accordance with claim 1, wherein the first receiving signal data record is recorded from a point in time that is arranged at a spaced location from the point in time of the transmitting pulse by a triggering delay.

5. A method in accordance with claim 1, further comprising the steps of:
   triggering a second ultrasonic pulse at the ultrasound transmitter by a generated transmitting pulse;
   sending a receiving signal by the ultrasound receiver;
   recording the receiving signal as a second receiving signal data record as a function of time after the transmitting pulse;
   forming a correlation function of the second receiving signal data record with the first sample data record; and
   scaling the first sample data record.

6. A method in accordance with claim 5, wherein the first sample data record is scaled in proportion to the ratio of the signal energies of the first and second receiving signal data records.

7. A method in accordance with claim 1, further comprising the steps of:
   triggering a second ultrasonic pulse at the ultrasound transmitter by a generated transmitting pulse;
   sending a receiving signal by the ultrasound receiver;
   recording the receiving signal as a second receiving signal data record as a function of time after the generated transmitting pulse;
   forming a correlation function of the second receiving signal data record with the second sample data record;
   using a section of the first receiving signal data record as a second sample data record, which is arranged at a spaced location from the point in time of transmitting the second ultrasonic pulse by the run time determined from the first receiving signal data record; and
   determining a run time of the second ultrasonic pulse from the point in time of the correlation maximum.

8. A method in accordance with claim 7, wherein the second receiving signal data record is recorded from a point in time that is arranged at a spaced location from the point in time of the generated transmitting pulse by a triggering delay.

9. A method in accordance with claim 1, further comprising the steps of:
   triggering another ultrasonic pulse at the ultrasound transmitter by a generated transmitting pulse;
   sending a receiving signal from the ultrasound receiver;
   recording the receiving signal as a delay-time receiving signal data record as a function of time after the transmitting pulse;
   determining a correlation function of the delay-time receiving signal data record with the delay-time sample data record;
   determining a time difference between the transmitting pulse and the first reception of the ultrasonic pulse from the point in time of a correlation maximum;
   determining a delay time between the transmitting pulse and the transmission of the ultrasonic pulse by subtracting the signal run time for the ultrasonic pulse along the length of the measuring section; and
   calculating a signal run time from the measuring section length.

10. A method in accordance with claim 9, wherein the delay-time sample data record is taken from the delay-time receiving signal data record.

11. A method in accordance with claim 10, wherein a maximum of the delay-time receiving signal data record is determined and the delay-time sample data record includes a section about the maximum.

12. A method in accordance with claim 1, further comprising the steps of:
   triggering another ultrasonic pulse at the ultrasound transmitter by a generated transmitting pulse;
   sending a receiving signal from the ultrasound receiver;
   recording the receiving signal as a measuring-section receiving signal data record as a function of time after the transmitting pulse,
   forming a correlation function of the measuring-section receiving signal data record;
   determining a time interval between the first reception of the ultrasonic pulse at the ultrasound receiver and the reception of the first echo of the ultrasonic pulse from an autocorrelation of the measuring-section receiving signal data record; and calculating a measuring section length from the time interval and the sound velocity.

13. A method in accordance with claim 1, further comprising the step of determining a temperature of the gas in the breathing gas volume flow sensor.

14. A gas flow velocity sensor comprising:
a flow duct having a measuring section arranged in parallel to or at an angle smaller than 90° to said flow duct;
an ultrasound transmitter at said measuring section;
an ultrasound receiver at said measuring section and spaced apart from said ultrasound transmitter with a flow path of said flow duct between said ultrasound transmitter and said ultrasound receiver;
a function generator generating a transmitting pulse triggering an ultrasonic pulse at said ultrasound transmitter such that said ultrasound receiver sends a receiving signal;
a signal processing unit receiving said receiving signal and recording same as a first receiving signal data record as a function of time after the transmitting pulse, forming a correlation function of the first receiving signal data record with a first sample data record and determining a run time of the ultrasonic pulse from the point in time of a correlation maximum.

15. A gas flow velocity sensor in accordance with claim 14, wherein the sample data record is taken from the first receiving signal data record and the maximum of the first receiving signal data record is determined and the sample data record includes a section around the maximum.

16. A gas flow velocity sensor in accordance with claim 14, wherein the first receiving signal data record is recorded from a point in time that is arranged at a spaced location from the point in time of the transmitting pulse by a triggering delay.

17. A gas flow velocity sensor in accordance with claim 14, wherein the function generator triggers a second ultrasonic pulse at the ultrasound transmitter by a generated transmitting pulse, a receiving signal is sent by the ultrasound receiver and the signal processing unit records the receiving signal as a second receiving signal data record as a function of time after the transmitting pulse, forms a correlation function of the second receiving signal data record with the first sample data record and scales the first sample data record in proportion to the ratio of the signal energies of the first and second receiving signal data records.

18. A gas flow velocity sensor in accordance with claim 14, wherein the function generator triggers a second ultrasonic pulse at the ultrasound transmitter by a generated transmitting pulse and the ultrasound receiver sends a receiving signal and the signal processing unit records the receiving signal as a second receiving signal data record as a function of time after the transmitting pulse, forms a correlation function of the second receiving signal data record with the second sample data record, uses a section of the first receiving signal data record as a second sample data record, which is arranged at a spaced location from the point in time of transmitting the ultrasonic pulse by the run time determined from the first receiving signal data record and determines a run time of the second ultrasonic pulse from the point in time of the correlation maximum, wherein the second receiving signal data record is recorded from a point in time that is arranged at a spaced location from the point in time of the transmitting pulse by a triggering delay.

19. A gas flow velocity sensor in accordance with claim 1, wherein the function generator triggers an ultrasonic pulse at the ultrasound transmitter by a generated transmitting pulse, the ultrasound receiver sends a receiving signal from the ultrasound receiver and the signal processing unit records the receiving signal as a delay-time receiving signal data record as a function of time after the transmitting pulse, determines a correlation function of the delay-time receiving signal data record with the delay-time sample data record, determines a time difference between the transmitting pulse and the first reception of the ultrasonic pulse from the point in time of a correlation maximum, determines a delay time between the transmitting pulse and the transmission of the ultrasonic pulse by subtracting the signal run time for the ultrasonic pulse along the length of the measuring section and calculates a signal run time from the measuring section length, wherein the delay-time sample data record is taken from the delay-time receiving signal data record.

20. A gas flow velocity sensor in accordance with claim 19, wherein a maximum of the delay-time receiving signal data record is determined and the delay-time sample data record includes a section about the maximum.

21. A gas flow velocity sensor in accordance with claim 14, wherein the function generator triggers an ultrasonic pulse at the ultrasound transmitter by a generated transmitting pulse, the ultrasound receiver sends a receiving signal and the signal processing unit records the receiving signal as a measuring-section receiving signal data record as a function of time after the transmitting pulse, forms a correlation function of the measuring-section receiving signal data record, determines a time interval between the first reception of the ultrasonic pulse at the ultrasound receiver and the reception of the first echo of the ultrasonic pulse from an autocorrelation of the measuring-section receiving signal data record and calculates a measuring section length from the time interval and the sound velocity.

22. A gas flow velocity sensor in accordance with claim 14, wherein a temperature of the gas in the breathing gas volume flow sensor is determined.

* * * * *